United States Patent [19]

Zolotarev et al.

[11] Patent Number: 5,026,909

[45] Date of Patent: Jun. 25, 1991

[54] METHOD FOR PREPARING BIOLOGICALLY ACTIVE ORGANIC COMPOUND LABELLED WITH HYDROGEN ISOTOPE

[76] Inventors: Jury A. Zolotarev, ulitsa Rogova, 16, korpus 1, kv. 168; Dmitry A. Zaitsev, ulitsa Rogova, 2, kv. 160; Vadim J. Tatur, ulitsa Novopetrovskaya, 17, kv. 15; Nikolai F. Myasoedov, ulitsa Narodnogo opolchenia, 5, korpus 2, kv. 117, all of Moscow, U.S.S.R.

[21] Appl. No.: 327,327

[22] Filed: Mar. 22, 1989

[51] Int. Cl.$^5$ .............................................. C07C 229/00
[52] U.S. Cl. .................................... 562/575; 530/329; 530/330; 530/331; 530/333; 536/26; 536/55.2; 548/303; 548/342; 548/344; 548/494; 548/496; 548/502; 548/504; 548/535; 562/443; 562/559; 562/567; 562/570; 562/574; 562/576; 564/463
[58] Field of Search .............. 562/575, 574, 443, 559, 562/570, 567, 576; 536/26, 55.2; 548/303, 535, 344, 494, 496, 502, 504, 342; 530/329, 330, 331, 333; 564/463

[56] References Cited

U.S. PATENT DOCUMENTS 3,976,689  8/1976  Reinhold ............................ 562/574
4,162,142  7/1979  Ehrenkaufer ....................... 562/575

OTHER PUBLICATIONS

Veres, Radiochemical Radioanalytical Letters, 46(5), pp. 307–316, (1981).
Ault, "Techniques and Experiments for Organic Chemistry", pp. 293–296, 4th Ed., (1983).
House, "Modern Synthetic Reactions", 2nd Ed., pp. 1–10, (1972).

Primary Examiner—Michael L. Shippen
Attorney, Agent, or Firm—Burgess, Ryan & Wayne

[57] ABSTRACT

A method according to the invention comprises mixing the starting biologically active organic compound, an inorganic vehicle and a catalyst in the form of a platinum-group metal, followed by reacting the resulting mixture with an isotope of hydrogen at a temperature of 373–523 K. and cooling the reaction mixture to a temperature of 288–303 K. and isolation of the desired product therefrom. The invention can be useful, for example, in medical and biological studies.

3 Claims, No Drawings

METHOD FOR PREPARING BIOLOGICALLY ACTIVE ORGANIC COMPOUND LABELLED WITH HYDROGEN ISOTOPE

FIELD OF THE INVENTION

The present invention relates to the art of organic biochemistry and, more specifically, to a method for preparing a biologically active organic compound labelled with an isotope of hydrogen. Such compounds are widely used, for example, in medical and biological studies.

BACKGROUND OF THE INVENTION

For the preparation of biologically active organic compounds labelled with hydrogen isotopes it is known to use liquid-phase catalytical reactions of hydrogenation of unsaturated starting compounds or of dehalogenation of halide derivatives of the starting compounds. This results in the preparation of hydrogen isotope-labelled compounds containing only 1-2 hydrogen isotopes.

The progress in molecular biology and genetics is defined to a great extent by the availability of biologically active organic compounds labelled with hydrogen isotopes, since these compounds are indispensible for, e.g. carrying out research at the level of cell receptors or in the radioimmune diagnosis.

In this respect especially important are versatile methods for the preparation of isotope-labelled compounds pertaining to different classes of biologically active organic compounds.

Known in the art is a method for producing an isotope-labelled biologically active organic compound, namely a biogenic amine which comprises preparation of a mixture of solution of a biogenic amine in water with an inorganic vehicle and a catalyst, followed by treatment of the resulting mixture at a temperature of 280-303 K. with a gaseous hydrogen isotope, in particular with tritium, and a subsequent recovery of the desired product from the reaction mixture. (Radiochemical Radioanalytical Letters, vol. 46, No. 5, 1981, K.Verše et al., "Tritiation of organic compounds by the CESG method", p.307-316).

However, the degree of incorporation of the isotope (in particular, the value of specific radioactivity proportional thereto) in the labelled compound obtained by this method is 30-500 TBq/mol which corresponds to less than 0.5 hydrogen isotope atom per molecule of the labelled compound. Therefore, prepared by this method are biogenic amines with a low degree of incorporation of the label of a hydrogen isotope (tritium) at a non-uniform distribution thereof within the labelled compound molecule.

Known in the art is a method for preparing a biologically active organic compound (such as a biogenic amine, aminoacids, components of nucleic acids and the like) labelled with hydrogen isotopes which comprises preparation of a mixture of a solution of the starting compound in water or in an organic solvent with an inorganic vehicle and a catalyst, treatment of the resulting mixture at a temperature of 288-303 K. with a gaseous hydrogen isotope such as tritium, followed by isolation of the desired product (Uspekhi Knimii, vol.50, iss. 2, 1981, Moscow, L. A. Neuman "Incorportion of tritium into biologically active compounds by exchange methods", pp. 210-213).

The labelled compound obtained by this method has a specific radioactivity of 30-500 TBq/mol. In this case the isotope label is included mainly at the most reactive hydrogen atoms of the prepared compound.

Therefore, this method also enables preparation of biologically active compounds with a low degree of inclusion of the label of a hydrogen isotope (tritium) at a non-uniform distribution thereof within the molecule of the labelled compound.

It is an object of the present invention to increase the degree of incorporation of a label of a hydrogen isotope in a labelled biologically active organic compound.

It is another object of the present invention to obtain a labelled biologically active organic compound with a uniform distribution of a hydrogen isotope label within the molecule of the labelled compound.

SUMMARY OF THE INVENTION

This object is accomplished by a method for preparing a biologically active organic compound labelled with hydrogen isotopes according to the present invention which comprises preparation of a mixture of the starting compound, an inorganic vehicle and a catalyst such as a platinum-group metal, reacting this mixture with a hydrogen isotope at a temperature of 373-523 K., followed by cooling the reaction mixture to a temperature of 288-303 K. and isolation of the desired product therefrom.

It is advisable to use, as the above-mentioned starting compound, a complex of the starting compound with a platinum-group metal.

In this case it is desirable to use a complex of a platinum-group metal with amines, aminoacids, sugars, aminosugars, peptides, purine and pyrimidine bases, nucleosides, carboxylic acids, nitrogen-containing derivatives of tetrahydrothiophene.

It is also advisable to use deuterium as the isotope of hydrogen.

The method for preparing a hydrogen isotopelabelled biologically active organic compound makes it possible to obtain labelled compounds with an increased degree of incorporation of an isotope label thereinto, and to obtain multi-labelled compounds with a uniform distribution of the isotope label within the molecule of the labelled compound.

The method according to the present invention is of a versatile character, since it can be used for the preparation of various biologically active compounds and does not necessitate the synthesis of unsaturated or halogen-containing starting compounds.

The method according to the present invention makes it possible to obtain optically active compounds multi-labelled with hydrogen isotopes.

Furthermore, in the case of producing peptides labelled with hydrogen isotopes the method according to the present invention makes it possible to obtain multi-labelled peptides of any chemical structure so that the isotope label is uniformly incorporated in all aminoacid residues with its predominant localization at the α-carbon atoms.

DETAILED DESCRIPTION OF THE INVENTION

The method for preparing a biologically active organic compound labelled with a hydrogen isotope according to the present invention is effected in the following manner.

The starting biologically active organic compound or a complex thereof with a platinum-group metal is mixed with an inorganic carrier and a catalyst in the form of a platinum group metal.

As the starting biologically active organic compound use can be made of, for example, amines, aminoacids, sugars, aminosugars, peptides, purine and pyrimidine bases, nucleosides, carboxylic acids, nitrogen-containing derivatives of tetrahydrothiophene and the like, while as the platinum-group metal use is made of, for example, platinum, palladium and the like.

The resulting mixture is reacted with a hydrogen isotope at a temperature 373–523 K., whereafter the reaction mixture is cooled to 288–303 K. and the desired product is recovered therefrom.

In this case as the isotope of hydrogen use is made of deuterium or tritium.

If the temperature of the reaction of said mixture with the hydrogen isotope is below 373 K., the degree of incorporation of the isotope label into the compound will be insufficient, whereas in the case of the reaction temperature exceeding 523 K. the resulting labelled compound will be decomposed.

Upon cooling of the reaction mixture to a temperature above 303 K. the decomposition of the reaction mixture is possible with a subsequent isolation of the desired product therefrom.

Cooling of the reaction mixture to a temperature below 288 K. is undesirable and necessitates additional expenses and time without giving any additional positive effect.

The desired product is isolated from the reaction mixture by extracting it with a solvent, followed by purification of the obtained product by, for example, chromatographic methods with subsequent chemical and radiochemical analyses of the thusobtained desired product.

For a better understanding of the present invention, some specific examples are given hereinbelow by way of illustration.

EXAMPLE 1

15.0 mg of a catalyst on a carrier in the form of a 5% palladium supported on calcium carbonate are mixed with 3.0 mg of a palladium-L-valine complex.

The mixture is placed into an ampule. The ampule is evacuated, filled with gaseous deuterium to the pressure of 0.04 MPa and heated to 493 K. The reaction mixture is kept till completion of the process of interaction of deuterium with L-valine and cooled to 293 K.

The desired product is isolated by means of a 0.1M solution of ammonium hydroxide and purified by way of liquid chromatography.

The chromatographic purification is effected on a carboxy cationite Emberlite CG 50 (III) in the form of copper. The degree of filling of the sorbent with copper ions is 70%. The eluent is a 0.2M ammonium hydroxide. Traces of copper ions are removed from the eluent by passing the latter through a chromatographic column of 15×10 mm size packed with a complex-forming sorbent Dowex A I. The fraction of L-valine is collected according to the readings of a UV-detector from 22 to 27 ml. The eluent is evaporated, L-valine is analyzed by means of chromatomass-spectrometry, column liquid chromatography on a chiral sorbent and by thin-layer chromatography.

To analyze the degree of substitution of hydrogen atoms with deuterium in a molecule of L-valine derivatization is effected by means of mass-spectrometry to give its trimethylsilyl derivative which is introduced into a chromatomass-spectrometer. In the case of L-valine the main peak (144 atom units) is shifted by 8 units to 152. The degree of substitution of stable hydrogen atoms with deuterium is 96.7%. The degree of substitution of α-hydrogen atoms is assessed by the ratio of peaks with the mass of 219 and 218 units and is equal to 96.4%.

Therefore, the degree of substitution in the α-position coincides with the degree of substitution in the remaining hydrocarbon portion of the molecule which points to the uniformity of distribution of the deuterium label over the amino acid molecule. The chemical yield of the amino acid and the optical purity are determined by means of a highly-effective liquid chromatography on a sorbent containing optically active groupings of L-hydroxyproline and filled with copper ions. The column is of 250×4 mm. The sorbent particle size is 5 μm. The eluent is a 0.01M ammonium acetate with the pH of 4.0 containing $1\times 10^{-4}$M of copper acetate (II).

L-valine is eluted from 18 to 22 ml; under these conditions the D-isomer should come out at the 27-th ml. The content of the L-isomer in the product is 98%. 1.0 mg of L-/$^2$H$_8$/ valine is obtained with the chemical yield of 69%.

The analysis for chemical purity is effected by means of thin-layer chromatography on "Silufol" in a system isopropanol-acetone-ammonia (15:9:9). The product is chromatographically homogeneous, no foreign matter is detected.

EXAMPLES 2 to 9

5.6 mg of a catalyst - palladium supported on calcium carbonate and 1.4 mg of rhodium-valine complex Rh(L-Val)Cl$_2$ are intermixed. Portions of 7 mg of the resulting mixture are placed into ampules, evacuated and filled with gaseous deuterium to the pressure of 0.026 MPa. The reaction of the mixture with deuterium is effected for 20 minutes at a temperature of 413 to 533 K. A further treatment is carried out as described in Example 1. The degree of incorporation of deuterium and the yield of the labelled amino acid are shown in Table 1 hereinbelow.

EXAMPLES 10 TO 15

Mixed are 1.4 mg of rhodium-valine complex Rh(L-Val)Cl$_2$ (4.3 μ-mol) and a variable (from 5 to 200 mg) amount of a catalyst containing 5% by mass of palladium supported on calcium carbonate, the mixture is homogenized in ampules and freezed with liquid nitrogen. Water is removed by lyophilic drying. The ampules are evacuated and filled with gaseous deuterium to the pressure of 0.026 MPa. The reaction with deuterium is conducted for 40 minutes at 473 K. The further treatment is carried out in a manner similar to that described in Example 1 hereinbefore. The degree of incorporation of deuterium, optical purity and yield of the amino acid are shown in Table 2 hereinbelow.

TABLE 1

| Solid-phase isotope exchange of gaseous deuterium with rhodium-valine complex | | | |
|---|---|---|---|
| Example No. | Temperature, K | Incorporation of deuterium, at/mol | Yield, % |
| 1 | 2 | 3 | 4 |
| 2 | 413 | 0.24 | 90 |
| 3 | 433 | 0.57 | 90 |
| 4 | 453 | 0.97 | 85 |

TABLE 1-continued

| Solid-phase isotope exchange of gaseous deuterium with rhodium-valine complex | | | |
|---|---|---|---|
| Example No. | Temperature, K | Incorporation of deuterium, at/mol | Yield, % |
| 1 | 2 | 3 | 4 |
| 5 | 473 | 1.97 | 85 |
| 6 | 493 | 2.85 | 80 |
| 7 | 513 | 4.0 | 65 |
| 8 | 523 | 4.8 | 40 |
| 9 | 533 | 4.9 | 10 |

EXAMPLE 16

Mixed are 5.6 mg of a 5% palladium supported on barium sulphate and 1.4 mg (4.3 μmol) of a rhodium-valine complex are intermixed as described in Example 2, placed into an ampule which is evacuated and filled with gaseous deuterium to the pressure of 0.026 MPa. The ratio between the amino acid and the catalyst is 1:10. The interaction with deuterium is conducted for 40 minutes at 473 K. The desired product is isolated and analyzed as described in Example 1. Obtained are 380 μg of L-valine with the chemical yield of 87% and incorporation of deuterium of 1.4 atom per molecule of the amino acid.

TABLE 2

| Incorporation of deuterium in L-valine depending on the aminoacid:catalyst ratio | | | | |
|---|---|---|---|---|
| Example No. | Ratio of the aminoacid to the catalyst | Incorporation of deuterium, at/mol | Yield, % | Optical density, % |
| 10 | 1:10 | 3.6 | 84 | 90 |
| 11 | 1:20 | 3.6 | 82 | 81 |
| 12 | 1:40 | 3.6 | 82 | 73 |
| 13 | 1:100 | 3.6 | 79 | 18 |
| 14 | 1:200 | 3.5 | 81 | 10 |
| 15 | 1:400 | 2.8 | 61 | 9 |

EXAMPLES 17 TO 19

5.6 mg of a 5% palladium supported on calcium carbonate and 4.3 μmol of valine complexes of rhodium (III) or palladium (II), or platinum (II) are intermixed as described in Example 2, placed into an ampule and filled with gasous deuterium to the pressure of 0,026 MPa. The ratio of the amino acid to the catalyst is 1:10. The reaction with deuterium is conducted for 40 minutes at 473 K. The incorporation of deuterium and the yield of the labelled amino acid are shown in the following Table 3.

TABLE 3

| Incorporation of deuterium in L-valine and the yield of L-valine depending on the nature of ion of the complex-forming agent | | | |
|---|---|---|---|
| Example No. | Ion of the complex-forming agent | Incorporation of deuterium, at/mol | Yield, % |
| 17 | rhodium (III) | 3.6 | 84 |
| 18 | platinum (II) | 4.5 | 70 |
| 19 | palladium (II) | 5.4 | 74 |

EXAMPLES 20 TO 33

5.6 mg of a 5% palladium supported on calcium carbonate and 1.4 mg of a rhodium-valine complex (4.3 μmol) are intermixed, the mixture is then placed into an ampule. The ampule is evacuated and filled with gaseous deuterium to the pressure of 0.026 MPa (127 μmol).

The further treatment and analysis of the desired product are carried out as described in Example 1 hereinbefore. The incorporation of deuterium at the temperatures of 433, 473 and 513 K. is shown in Table 4.

EXAMPLES 34 to 42

5.6 mg of a 5% palladium supported on calcium carbonate and 4.3μmol of rhodium complexes (III) with amino acids are intermixed and the mixture is placed into an ampule. The ampule is evacuated and filled with gaseous deuterium to the pressure of 0.026 MPa (127 μmol). The reaction mixture is maintained for 60 minutes at 473 K. The treatment procedure is similar to that of Example 1. The yield of the labelled amino acids and incorporation of deuterium into the amino acid molecule are shown in Table 5 hereinbelow.

EXAMPLES 43 TO 46

5.6 mg of a 5% palladium supported on calcium carbonate and 1.2 mg (34.3 μmol) of a palladium-valine complex are intermixed and placed into ampules. The ampules are evacuated and filled with gaseous deuterium to the pressure of 0.025 MPa (127 μmol). The mixture is maintained at the temperature of 493 K. and then treated following the procedure described in Example 1 hereinbefore. The obtained data are shown in Table 6 hereinbelow.

In Example 46 the gaseous deuterium is changed after 10 minutes of the reaction and the mixture is maintained for additional 10 minutes.

EXAMPLE 47 TO 56

5.6 mg of a 5% palladium on barium carbonate and 4.3 μmol of L-leucine complexes of rhodium (III) and palladium (II) are intermixed as described in Example 2, the mixture is placed into an ampule and filled with gaseous deuterium to the pressure of 0.026 MPa (127 μmol). The interaction with deuterium is conducted for 2 hours at the temperature of 453 K. The desired product is isolated and treated as described in Example 1 hereinbefore. The incorporation of deuterium and the yield of the labelled aminoacid are shown in the following Table 7.

EXAMPLE 57

Placed into an ampule are 21 mg of a mixture consisting of 10 mg of alumina, 1 mg of biotin and 10 mg of a catalyst containing a 5% by mass of palladium supported on calcium carbonate prepared as described in Example 1 hereinbefore. The ampule is evacuated to the residual pressure of $10^{-3}$ HPa and filled with gaseous tritium to the pressure of 400 HPa. The ampule is heated for 40 minutes at the temperature of 473 K., then cooled to 288 K. and the desired product is isolated. The reaction mixture is suspended in 3.0 ml of a solvent consisting of 1 part of a 0.1M ammonium hydroxide and 2 parts of methanol. The catalyst and the substrate are removed by centrifugation, the solution is evaporated under a reduced pressure to remove the labile tritium, the reaction products are dissolved in 150 μl of the eluent and chromatography is then conducted on the sorbent "Ultrasphere ODS-5 μm".

TABLE 4

Incorporation of deuterium in L-valine vs. temperature and duration of the reaction

| | Time, minutes | | | | |
|---|---|---|---|---|---|
| | 10 | 20 | 40 | 80 | 160 |
| 1 | 2 | 3 | 4 | 5 | 6 |
| Example No. (at 433 K) | 20 | 21 | 22 | 23 | 24 |
| Incorporation of deuterium, at/mol | 0.3 | 0.57 | 1.0 | 1.35 | 1.53 |
| Yield, % | 90 | 90 | 90 | 90 | 90 |
| Example No. (at 473 K) | 25 | 26 | 27 | 28 | 29 |
| Incorporation of deuterium, at/mol | 1.06 | 1.97 | 3.62 | 4.6 | 5.4 |
| Yield, % | 90 | 85 | 70 | 60 | 50 |
| Total degree of substitution of hydrogen atoms with deuterium, % | 13 | 25 | 45 | 57 | 68 |
| Degree of substitution of hydrogen atoms with deuterium in the α-position, % | 12 | 23 | 41 | 52 | 65 |
| Example No. (at 513 K) | 30 | 31 | 32 | 33 | |
| Incorporation of deuterium, at/mol | 3.0 | 4.6 | 5.2 | 5.5 | |
| Yield, % | 80 | 65 | 50 | 30 | |

TABLE 5

Incorporation of deuterium into aminoacids

| Example No. | Aminoacid | Incorporation of deuterium, at/mol | Degree of substitution of hydrogen atoms for deuterium, % | Optical purity, % | Yield, % |
|---|---|---|---|---|---|
| 34 | α-Alanine | 2.71 | 68 | 90 | 80 |
| 35 | Glycine | 1.67 | 84 | — | 75 |
| 36 | Serine | 1.71 | 57 | 85 | 70 |
| 37 | Threonine | 3.14 | 63 | 85 | 70 |
| 38 | Valine | 4.40 | 55 | 90 | 80 |
| 39 | β-Alanine | 3.05 | 76 | — | 85 |
| 40 | α-Aminobutyric acid | 4.77 | 79 | 90 | 80 |
| 41 | Proline | 5.47 | 78 | 99 | 90 |
| 42 | Isoleucine | 5.06 | 51 | 90 | 80 |

TABLE 6

Incorporation of deuterium in L-valine

| Example No. | Time, minutes | Degree of incorporation of deuterium, at/mol | Degree of substitution of hydrogen atoms with deuterium, % | Yield, % | Optical purity, % |
|---|---|---|---|---|---|
| 43 | 10 | 5.25 | 66 | 78 | 99 |
| 44 | 20 | 5.50 | 69 | 76 | 99 |
| 45 | 40 | 5.60 | 70 | 72 | 99 |
| 46 | 10.10 | 6.90 | 86 | 76 | 99 |

TABLE 7

Incorporation of deuterium in L-leucine

| Example No. | Temperature, K | Complex-forming ion | Incorporation of deuterium, at/mol | Yield, % | Optical purity, % |
|---|---|---|---|---|---|
| 1 | 2 | 3 | 4 | 5 | 6 |
| 47 | 453 | rhodium | 2.7 | 86 | 93 |
| 48 | 453 | palladium | 4.2 | 82 | 99 |
| 49 | 453 | palladium | 4.5 | 90 | 99 |
| 50 | 473 | palladium | 6.2 | 83 | 94 |
| 51 | 493 | palladium | 7.2 | 71 | 86 |
| 52 | 513 | palladium | 7.8 | 40 | 63 |
| 53 | 453 | rhodium | 3.2 | 90 | 98 |
| 54 | 473 | rhodium | 4.9 | 85 | 95 |
| 55 | 493 | rhodium | 5.0 | 65 | 82 |
| 56 | 513 | rhodium | 5.0 | 35 | 60 |

As the eluent use is made of a solvent containing 20% by volume of methanol, 0.4% by volume of triethylamine trifluoroacetate and 0.1% by volume of monosodium phosphate. The acidity is 4.0. The rate of the eluent supply is 1.2 ml/min, pressure 16.0 MPa. Use is made of a UV-sensor with the working wavelength of 220 nm. The tritium-labelled biotin is eluted at the 15-th ml in the volume of 3 ml. The eluent is evaporated to dryness under a reduced pressure, the product is dissolved in a 50% aqueous ethanol to the radioactive concentration of 37 TBq/l. There are obtained 122 μg (0.60 μmol) of tritium-labelled biotin with the chemical yield of 12.2%, specific radioactivity of 1,600 TBq/mol in the amount of 800 MBq. According to the results of a highly effective liquid chromatography, the radiochemical purity of (G-$^3$H)-biotin is over 98%.

EXAMPLE 58

Placed into an ampule are 21 mg of a mixture consisting of 10 mg of alumina, 1 mg of adenosine and 10 mg of a catalyst - a 5% palladium supported on calcium carbonate, the mixture is prepared as described in Example 1. The ampule is evacuated to the residual pressure of $10^{-3}$ HPa and filled with gaseous tritium to the pressure of 400 HPa and then heated for 40 minutes at the temperature of 473 K.

The reaction mixture cooled to 303 K. is suspended in 3.0 ml of a solvent consisting of 5 parts of a 0.02M hydrochloric acid and 1 part of methanol. The catalyst and alumina substrate are separated by centrifugation, the solution is evaporated under a reduced pressure.

The reaction products are dissolved in 150 μl of an eluent and chromatography is then effected on a sorbent Ultrasphere ODS-5 μm. As the eluent uese is made of a solvent containing 6% by volume of methanol and 0.4% by volume of monosodium phosphate. The eluent acidity is 4.0. The rate of the eluent supply is 1.5 ml/min, a UV spectrophotometric sensor with the working wavelengths of 254 and 280 nm is used. Tritium-labelled adenosine is eluted at the 20-th ml in the volume of 2.5 ml. The eluent is evaporated to dryness under a reduced pressure, the product is dissolved in a 50% aqueous ethanol to the radioactive concentration of 37 GBq/l.

There are thus obtained 30.7 μg (0.11 μmol) of tritium-labelled adenosine with the chemical yield of 3.1%, specific radioactivity of 4,000 TBq/mol in the amount of 455 MBq. The UV-spectrum of the tritium-labelled product fully corresponds to adenosine of a normal isotope composition. According to the results of a highly-effective liquid chromatography the radiochemical purity of (G-$^3$H'-adenosine is above 98%.

EXAMPLES 59-60

21 mg of a mixture consisting of 10 mg of alumina, 1 mg of adenosine and 10 mg of a catalyst containing 5% of palladium supported on calcium carbonate and prepared as described in Example 1 hereinbefore are placed into an ampule. The treatment is carried out as described in Example 58. The results of analysis of the desired product are shown in the following Table 8.

TABLE 8

| Example No. | Temperature, K | Incorporation of tritium, atom/ml | Specific radioactivity, TBq/mol | Yield, % |
| --- | --- | --- | --- | --- |
| 59 | 433 | 2.03 | 2,180 | 50.0 |
| 60 | 453 | 2.86 | 3,070 | 13.2 |
| prior art | 293 | 0.3 | 330 | 40.0 |

EXAMPLE 61

Placed into an ampule are 16 mg of a mixture consisting of 10 mg of alumina, 1.0 mg of phenylalanine and 5.0 mg of a catalyst - 5% palladium supported on calcium carbonate, the mixture is prepared as described in Example 1 hereinbefore. The ampule is evacuated and filled with gaseous tritium to the pressure of 400 HPa. The ampule is heated for 40 minutes at the temperature of 473 K. The cooled reaction mixture is suspended in 3.0 ml of a 0.1M ammonium hydroxide. The catalyst and the alumina support are separated by centrifugation, the solution is evaporated for 2 times with a 0.1M ammonia to remove labile tritium.

The reaction products are dissolved in 200 µl of a 0.1M ammonium hydroxide and chromatography is then effected on a sorbent Amberlite CG 50 (III) in the copper form. The sorbent filling with copper ions is 70%, the eluent is a 0.2M ammonium hydroxide. Tritium-labelled phenylalanine is eluted at the 18-th ml in the volume of 6 ml. Copper ions are removed from the product on a complex-forming sorbent Dowex AI and evaporation is effected under a reduced pressure. The product is dissolved in a 50% aqueous ethanol to the radioactive concentration of 37 GBq/l.

There are thus obtained 350 µg of (G-$^3$H)-phenylalanine with the specific radioactivity of 3,030 TBq/mol.

EXAMPLES 62 to 69

21 mg of a mixture consisting of 10 mg of alumina, 1 mg of L-methionine and 10 mg of a catalyst - 5% rhodium supported on alumina are placed into an ampule. The treatment is carried out as described in Example 61 hereinabove. The results of analysis of the desired product are shown in Table 9 hereinbelow.

EXAMPLE 70

Placed into an ampule are 21 mg of a mixture consisting of 10 mg of a lyophilically dried alumina, 1 mg of glucosamine and 10 mg of a catalyst containing 5% palladium supported on calcium carbonate, the mixture is prepared as described in Example 1 hereinbefore. The ampule is evacuated to the residual pressure of $10^{-3}$ HPa and filled with gaseous tritium to the pressure of 400 HPa. The ampule is heated for 30 minutes at the temperature of 453 K.

TABLE 9

| Example No. | Temperature, K | Incorporation of tritium, atom/mol. | Specific radioactivity, TBq/mol | Yield, % |
| --- | --- | --- | --- | --- |
| 1 | 2 | 3 | 4 | 5 |
| 62 | 373 | 0.01 | 11 | 100 |
| 63 | 393 | 0.04 | 41 | 100 |
| 64 | 413 | 0.16 | 170 | 100 |
| 65 | 433 | 1.4 | 444 | 85 |
| 66 | 453 | 1.5 | 1.600 | 32 |
| 67 | 473 | 3.1 | 3.300 | 15 |
| 68 | 493 | 3.1 | 90 | 3 |
| 69 | 513 | — | — | 0 |

The cooled reaction mixture is suspended in 3.0 mg of a 0.1M ammonium hydroxide. The catalyst and the substrate are separated by centrifugation, the solution is evaporated under a reduced pressure to remove labile tritium. The reaction products are dissolved in 150 µl of an eluent: acetonitrile-water in the ratio of 6:1 and chromatography is then carried out on an aminopropyl sorbent with the particle size of 5 µm. The eluent is evaporated to dryness under a reduced pressure, the product is dissolved in a 50% aqueous ethanol to the radioactive concentration of 37 GBg/l. There are thus obtained 62 µg of tritium-labelled (G-$^3$H)-glucosamine with the specific radioactivity of 3,400 TBq/mol and the chemical yield of 6.2%.

EXAMPLE 71

Placed into an ampule are 11 mg of a mixture consisting of 5.0 mg of calcium carbonate, 0.5 mg of L-histidine and 5.5 mg of a catalyst - a 5% palladium on barium sulphate, the mixture is prepared as described in Example 1 hereinbefore. The ampule is evacuated and filled with gaseous tritium to the pressure of 250 HPa. The ampule is heated for 20 minutes at the temperature of 493 K. The reaction mixture is suspended in 1.5 ml of a 0.1M ammonium hydroxide. The catalyst and calcium carbonate are separated by centrifugation, the solution is twice evaporated with a 0.1M ammonium hydroxide to remove labile tritium. The further treatment is conducted as described in Example 61.

There are obtained 86 mCi of L-(2,3,2',5'-$^3$H)-histidine with the specific radioactivity of 4,600 TBq/mol which corresponds to the 86% substitution of hydrogen with tritium and incorporation of 4.3 atoms of tritium per molecule of the aminoacid. The chemical yield is 20%, the radiochemical purity is 98%, optical purity is 80%. According to the PMR data the tritium label is uniformly distributed over all carbon-hydrogen bonds.

EXAMPLES 72 to 75

Placed into an ampule are 11 mg of a mixture consisting of 5.0 mg of alumina, 0.5 mg of hexadecylamine ($C_{16}H_{33}NH_2$) or 0.5 mg of stearic acid ($C_{17}H_{35}CO_2H$) and 5.5 mg of a heterogeneous palladium catalyst.

The conditions for the preparation of the mixture and its interaction with tritium are the same as those described in Example 71 hereinbefore. The results of analysis of the desired product are shown in the following Table 10.

TABLE 10

| Example No. | Catalyst | Compound | Radio-activity, MBq | Specific radio-activity, TBq/mol | Yield, % |
|---|---|---|---|---|---|
| 72 | 5% Pd/BaSO$_4$ | C$_{16}$H$_{33}$NH$_2$ | 5,200 | 17,700 | 15 |
| 73 | 10% Pd/C | C$_{16}$H$_{33}$NH$_2$ | 6,600 | 31,400 | 9 |
| 74 | 5% Pd/BaCO$_3$ | C$_{17}$H$_{35}$CO$_2$H | 5,900 | 18,500 | 20 |
| 75 | 10% Pd/C | C$_{17}$H$_{35}$CO$_2$H | 6,300 | 30,000 | 14 |

EXAMPLES 76 to 79

Shown in Table 11 are Examples (76 through 79) illustrating preparation of tritium-labelled alanine, indolylacetic acid, tryptophane, tryptamine upon interaction with tritium at the temperature of 473 K. under the conditions of Example 61.

TABLE 11

| Example No. | Compound | Specific radioactivity, TBq/mol | Yield, % |
|---|---|---|---|
| 76 | L-(2,3-G-$^3$H)-alanine | 2,400 | 90 |
| 77 | (G-$^3$H)-indolylacetic acid | 3,000 | 32 |
| 78 | (G-$^3$H)-tryptophane | 2,700 | 50 |
| 79 | (G-$^3$H)-tryptamine | 2,500 | 60 |

EXAMPLE 80

Placed into an ampule is a mixture consisting of 6.2 mg (5.5 μmol) of a rhodium complex of a peptide-analog of naturally-occurring adrenocorticotrophic hormone (ACTH) - (Met-Glu-His-Phe-Pro-Gly-Pro) and 20 mg of a catalyst - 5% palladium supported on barium sulphate, the mixture is prepared as described in Example 1.

The ampule is evacuated to the pressure of $10^{-3}$ HPa and filled with gaseous tritium to the pressure of 400 HPa. The reaction mixture is heated to the temperature of 413 K. and maintained at this temperature for 2 hours. On completion of the reaction the mixture is cooled to 288 K. and gaseous tritium is removed; the reaction mixture is washed twice on the filter with 10 ml of methanol. The combined filtrate is evaporated and dissolved in 1 ml of a 50% methanol.

The desired product is isolated by way of a liquid chromatography. The eluent is an aqueous solution of a 11.5% secondary propanol containing 0.1% trifluoroacetic acid. The fraction containing the tritium-labelled peptide is dried and diluted with methanol to the radioactive concentration of 37 GBq/l.

According to the data of chromatographic and scintillation analyses there are determined the chemical yield of the product, its total radioactivity and specific radioactivity. There are thus obtained 3,000 μg of the tritium-labelled peptide with the total radioactivity of 5.55 GBq (150 ml) and with the specific radioactivity of 1,690 TBq/mol, The chemical yield of the desired product is 60%.

EXAMPLE 81

Charged into an ampule are 405 mg of a mixture containing 5.2 mg (6 μmol) of a rhodium complex of a peptide DAGO pertaining to the series of encephalins (Tyr-D-Ala-Gly-Phe-Gly(OH) and 400 mg of a catalyst - a 5% palladium supported on barium sulphate, the mixture is prepared as described in Example 1 hereinbefore. The ampule is evacuated to the pressure of $10^{-3}$ HPa and filled with gaseous tritium to the pressure of 400 HPa. The reaction with tritium is carried out at the temperature of 413 K. for 40 minutes. Then the reaction mixture is cooled to 304 K., gaseous tritium is removed and the reaction mixture is washed on the filter with two portions by 10 ml of a 20% aqueous solution of ethanol containing 0.2% of ammonium hydroxide. The combined filtrate is evaporated and dissolved in 1 ml of a 50% aqueous solution of methanol.

The product is purified by way of a highly effective liquid chromatography on a column packed with a modified silica gel containing octadecyl groupings C$_{18}$ (Serva, 4.6×250 mm). As the eluent use is made of a 60% aqueous solution of methanol containing 0.1% trifluoroactic acid.

There are obtained 1,120 μg (2.19 μmol) of the tritium - labelled peptide with the total radioactivity of 3.81 GBq (103 mCi), specific radioactivity of 1,780 TBq/mol. The chemical yield of the product is 28%.

EXAMPLE 82

Charged into an ampule are 17 mg of a mixture consisting of 16.8 mg (13.3 μmol) of a rhodium complex of a peptide pertaining to the series of encephalins (Tyr-DAla-Gly-Phe-Leu-Arg) and 400 mg of a catalyst - palladium supported on barium sulphate, the mixture is prepared as in Example 80.

The reaction of interaction with tritium is conducted at the temperature of 413 K. for one hour. The peptide is isolated and purified as described in Example 81 hereinbefore.

There are thus obtained 7,420 μg (7.18 μmol) of the tritium-labelled peptide with the total radioactivity of 13.2 GBq (360 mCi) with the specific radioactivity of 1,850 TBq/mol and with the chemical yield of 54%.

EXAMPLE 83

417 mg of a mixture consisting of a complex of a peptide (Tyr-DAla-Gly-Phe-Leu-Arg) with rhodium and a catalyst - palladium supported on barium sulphate, the mixture being prepared as described in Example 82, are heated at the temperature of 453 K. under the conditions of Example 80.

There are thus obtained 980 μg of the tritium-labelled peptide with the total radioactivity of 4.54 GBq (122 mCi) and specific radioactivity of 4,880 TBq/mol, with the chemical yield of 7%. The substitution of hydrogen with tritium is 4.56 atoms per molecule of the peptide.

EXAMPLE 84

Charged into an ampule are 111 mg of a mixture prepared as described in Example 80 hereinbefore and consisting of 11 mg (10 μmol) of a complex of a peptide pertaining to the series of encephalins (Tyr-DAla-Gly-Phe-DLeu) and a catalyst containing 50 mg of a 5% palladium on barium sulphate and 50 mg of a 5% rhodium supported on calcium carbonate.

The peptide is produced, isolated and purified as described in Example 81 using, as the eluent, a 70% aqueous methanol containing 0.1% by volume of trifluoroacetic acid.

There are thus obtained 2,260 μg (3.01 μmol) of the tritium-labelled peptide with the total radioactivity of 5.03 BGq (136 mCi), specific radioactivity of 1.670 TBq/mol and with the chemical yield of 34%.

EXAMPLE 85

Charged into an ampule are 108 mg of a mixture prepared as in Example 80 hereinbefore consisting of 8.2 mg of a rhodium complex with a peptide of leucine-encephalin (Tyr-Gly-Gly-Phe-Leu) and a catalyst—a 5% palladium supported on barium sulphate. The further treatment of the resulting mixture is carried out as described in Example 80. The desired product is isolated and purified by chromatography on a column "Ultrasphere ODS" (150×4.6 mm, 5 μm). As the eluent use is made of a 60% aqueous methanol containing 0.2 vol. % of trifluoroacetic acid.

There are obtained 2,360 μg (3.8 μmol) of the tritium - labelled peptide with the total radioactivity of 5.89 GBq (160 mCi), specific radioactivity of 1,550 TBq/mol and with the chemical yield of 38%.

EXAMPLE 86

Charged into an ampule are 154 mg of a mixture consisting of 12 mg (4.5 μmol) of a platinum complex of a peptide (Gly-Leu-Leu-Asp-Ley-Lys), 11,200 μg (27 μmol) and 140 mg of a catalyst-rhodium supported on alumina. The reaction mixture is prepared as described in Example 80 hereinbefore. The reaction is conducted upon interaction with tritium for one hour.

The peptide is recovered and purified by chromatography in a column.

There are obtained 1,770 μg (2.67 μmol) of the tritium-labelled peptide with the total radioactivity of 4.3 GBq (116 mCi), specific radioactivity of 1,610 TBq/mol and with the chemical yield of 59%.

EXAMPLE 87

Charged into an ampule are 206 mg of a mixture prepared as described in Example 80 and consisting of 6.0 mg (5.2 μmol) of a peptide (Tyr-Ala-Gly-Phe-Tyr-Pro) and 200 mg of a catalyst—a 5% palladium supported on barium sulphate. The reaction mixture is prepared as described in Example 80. The reaction is conducted at the temperature of 413 K. for 2 hours. The peptide is isolated and purified by a column chromatography. As the eluent use is made of a 40% aqueous acetonitrile containing 0.05% by volume of trifluoroacetic acid.

There are obtained 1,100 μg (1.15 μmol) of the tritium - labelled peptide with the total radioactivity of 1.86 GBq (50 mCi), specific radioactivity of 1,630 TBq/mol and with the chemical yield of 22%.

EXAMPLE 88

Charged into an ampule are 412 mg of a mixture prepared as described in Example 80 consisting of 12 mg (9.5 μmol) of a rhodium complex of a peptide (Thre-Lys-Pro-Arg-Pro-Gly-Pro) and 400 mg of a catalyst - palladium-supported on barium sulphate. The reaction mixture is prepared as described in Example 80. The reaction is conducted at the temperature of 413 K. for 1 hour. The peptide is isolated and purified by a column chromatography using, as the eluent, a 60% aqueous methanol containing 1 mmol of tributylammonium trifuloroacetate, pH of the eluent is 2.2. There are obtained 2,200 μg (1.9 μmol) of the tritium-labelled peptide with the total radioactivity of 3.7 GBq/ (100 mCi), specific radioactivity of 1,960 TBq/mol and with the chemical yield of 20%.

EXAMPLE 89

Charged into an ampule are 246 mg of a mixture produced as described in Example 80 hereinbefore consisting of 16 mg (15 μmol) of a rhodium complex of a peptide (Tyr-Pro-Arg), 10,000 μg (15 μmol) of rhodium chloride and 130 mg of a 5% palladium supported on barium sulphate. The reaction mixture is prepared as described in Example 80. The reaction is conducted at the temperature of 443 K. for one hour. The peptide is recovered and purified by a column chromatography in a system of a 30% aqueous solution of methanol containing 0.1% by volume of trifluoroacetic acid.

There are obtained 1,500 μg of the tritium-labelled peptide with the total radioactivity of 6.7 GBq (181 mCi), specific radioactivity of 1,940 TBq/mol and with the chemical yield of 23%.

EXAMPLES 90 to 98

146 mg of the mixture described in Example 87 hereinbefore and containing a complex of the peptide Tyr-Pro-Arg with rhodium and a catalyst—a 5% palladium supported on barium sulphate is heated with tritium under the conditions described in the foregoing Example 88 at different temperatures. The results obtained are shown in Table 12 hereinbelow.

TABLE 12

Effect of the reaction temperature on the yield and substitution of hydrogen atoms in the peptide ($^3$H) Tyr—Pro—Arg during the reaction time of 1 hour

| Example No. | Temperature, K | Yield, % | Incorporation of tritium, % | Substitution of hydrogen, % |
|---|---|---|---|---|
| 1 | 2 | 3 | 4 | 5 |
| 90 | 373 | 64 | 16 | 0.29 |
| 91 | 393 | 60 | 21 | 0.38 |
| 92 | 403 | 62 | 34 | 0.61 |
| 93 | 413 | 56 | 38 | 0.69 |
| 94 | 423 | 58 | 68 | 1.23 |
| 95 | 433 | 31 | 85 | 1.54 |
| 96 | 443 | 21 | 100 | 1.81 |
| 97 | 453 | 8 | 106 | 1.92 |
| 98 | 473 | 0 | — | — |

EXAMPLE 99

Into an ampule there are placed 5.5 mg of a mixture produced as described in Example 20 consisting of 0.5 mg of L-valine and 5.0 mg of a catalyst—a 5% palladium supported on calcium carbonate. The ampule is evacuated to the pressure of $10^{-3}$ HPa and filled with gaseous tritium to the pressure of 400 HPa. The ampule is heated at the temperature of 493 K. for 30 minutes.

The reaction mixture is suspended in 3.0 ml of a 0.1M ammonium hydroxide. The catalyst is separated by centrifugation, the solution is twice evaporated to dryness with a 0.1M ammonium hydroxide to remove labile tritium and dissolved in 150 μl of a 0.1M ammonium hydroxide.

The chromatographic purification is conducted on a carboxy cationite Amberlite CG50(III) in the copper form. The degree of filling of the sorbent with copper ions is 70%. The eluent is a 0.2M ammonium hydroxide.

15

Use is made of a UV directflow sensor with a column of 15×10 mm placed after its measuring cuvette to remove traces of copper from the eluent and packed with a complex-forming sorbent "Dowex A-1". The fraction of L-valine is collected from the 20-th through the 26-th ml. The eluent is evaporated, L-valine is dissolved in a 50% aqueous ethanol and the radioactive concentration is brought to 37 GBq/l. There are obtained 2,400 MBq of (2,3,4,5-$^3$H)-valine with the specific radioactivity of 6,300 TBq/mol. The chemical yield is 8.9%. Analysis of the radiochemical purity is conducted by means of a thin-layer chromatography on "Silufol" in a system isopropanol-acetone-ammonia (15:9:9). The mobility of valine is 0.45. The radiochemical purity is 98%. Analysis of the optical purity is effected by means of a column ligand-exchange chromatography on a chiral sorbent, the optical purity is equal to 17%.

EXAMPLES 100 TO 105

Placed into an ampule are 10 mg of a mixture consisting of 10 mg of a catalyst containing 5% by mass of palladium supported on calcium carbonate and 1 mg of L-valine. The ampule is evacuated and filled with tritium to the pressure of 400 HPa.

The process of an isotope exchange and recovery of the tritium-labelled valine is conducted as described in Example 99. The relationship between the incorporation of tritium and temperature of the isotope exchange is shown in Table 13.

TABLE 13

| Example No. | Temperature, K | Specific radioactivity TBq/mol | Yield, % | Incorporation of tritium, atom/mol |
|---|---|---|---|---|
| 100 | 433 | 810 | 85 | 0.75 |
| 101 | 453 | 3,070 | 65 | 2.9 |
| 102 | 473 | 5,200 | 18 | 4.8 |
| 103 | 493 | 6,300 | 10 | 5.9 |
| 104 | 513 | 7,000 | 8 | 6.5 |
| 105 | 533 | — | 0 | — |

EXAMPLE 106 TO 109

Placed into an ampule are 11 mg of a mixture consisting of 10 mg of a catalyst containing 5% by mass of palladium supported on calcium carbonate and 1 mg of L-aminoacid. The ampule is evacuated and filled with tritium to the pressure of 400 HPa. The reaction is conducted at the temperature of 473 K. for 30 minutes. The results of the reaction of an isotope exchange are shown in the following Table 14.

TABLE 14

| Example No. | Aminoacids | Specific radioactivity, TBq/mol | Yield, % |
|---|---|---|---|
| 106 | Leucine | 6,700 | 13 |
| 107 | Proline | 5,600 | 14 |
| 108 | Threonine | 3,300 | 12 |

TABLE 14-continued

| Example No. | Aminoacids | Specific radioactivity, TBq/mol | Yield, % |
|---|---|---|---|
| 109 | Isoleucine | 6,500 | 13 |

EXAMPLE 110

Placed into an ampule are 6 mg of a mixture containing 5 mg of a catalyst - a 10% of palladium supported on carbon and 1 mg of L-valine. The ampule is evacuated and filled with tritium to the pressure of 350 HPa. The reaction is conducted at the temperature of 473 K. for 40 minutes. The recovery of the product is effected as described in Example 99 hereinbefore to give 120 μg of L-valine with the specific radioactivity of 4,800 TBq/mol and with the chemical yield of 12%.

EXAMPLE 111

Placed into an ampule are 12 mg of a mixture consisting of 2 mg of a complex of histamine-K$_2$-PtCl$_4$ and 10 mg of a catalyst - a 5% rhodium on alumina. The ampule is set under vacuum to the pressure of $10^{-3}$ HPa and filled with gaseous tritium to the pressure of 300 HPa. The ampule is heated for one hour at the temperature of 413 K.

The reaction mixture is suspended in 3.0 ml of a mixture of equal volumes of a 0.01M hydrochloric acid and ethanol. The catalyst is separated by centrifugation, the solution is evaporated to dryness to remove the labile tritium. The reaction products are dissolved in 200 μl of ammonium hydroxide.

The chromatographic purification is conducted on a carboxy cationite Amberlite CG 50 (III) in the copper form. The degree of filling of the sorbent with copper is 15%, the eluent is a 0.1M ammonium hydroxide. Use is made of a UV sensor with a column of 15×10 mm placed after its measuring cuvette to remove copper ions from the product and packed with a complex-forming sorbent Dowex A-1. The fraction containing histamine is collected from the 28-th through the 33-rd ml. The eluent is evaporated, the biogenic amine is dissolved in a 50% aqueous ethanol and the radioactive concentration is brought to 37 GBq/mol to give 2,400 MBq of (G-$^3$H)-histamine with the specific radioactivity of 1,700 TBq/mol. The chemical yield of the biogenic amine is 37%. The radiochemical purity analysis is carried out on a column "Ultrasphere ODS" in a system of 0.01M trifluoroacetic acid-acetonitrile. The radiochemical purity is equal to 98%.

EXAMPLES 112 to 135

The effect of the reaction temperature, nature of the metal of the complex-forming agent and of the catalyst is shown in Table 15 hereinbelow. The reaction, recovery and analysis of the product are shown as described in Example 111.

TABLE 15

| | Preparation of tritium-labelled biogenic amines by a solid-phase isotope exchange with gaseous tritium | | | | | |
|---|---|---|---|---|---|---|
| | | | | Complex-forming salt K$_2$PtCl$_4$ Temperature, K | | |
| NN | Amine | Catalyst | | 373 | 393 | 413 |
| 1 | 2 | 3 | | 4 | 5 | 6 |
| 1. | Histamine 5% | Rh/Al$_2$O$_3$ | Example | 112 | 113 | 114 |

TABLE 15-continued

| | | | Preparation of tritium-labelled biogenic amines by a solid-phase isotope exchange with gaseous tritium | | | |
|---|---|---|---|---|---|---|
| | | | Yield, % | 37 | 26 | 24 |
| | | | Specific radioactivity, TBq/mol | 740 | 1,300 | 1,700 |
| 2. | Tryptamine 5% | Rh/Al$_2$O$_3$ | Example | 122 | | |
| | | | Yield, % | 6 | | |
| | | | Specific radioactivity, TBq/mol | 670 | | |
| 3. | Tryptamine 5% | Pd/BaSO$_4$ | Example | 125 | 126 | 127 |
| | | | Yield, % | 80 | 60 | 54 |
| | | | Specific radioactivity, TBq/mol | 90 | 180 | 1,260 |

| | Complex-forming salt | | | | | | |
|---|---|---|---|---|---|---|---|
| | K$_2$PtCl$_6$ | | | | RhCl$_3$ | | |
| | Temperature, K | | | | | | |
| No.No. | 453 | 473 | 373 | 413 | 453 | 373 | 413 | 453 |
| 1 | 7 | 8 | 9 | 10 | 11 | 12 | 13 | 14 |
| 1 | 115 | 116 | 117 | 118 | — | 119 | 120 | 121 |
| | 1.5 | 0 | 40 | 15 | — | 32 | 12 | 4 |
| | 1,900 | — | 300 | 1,300 | | 670 | 1,100 | 2,000 |
| 2 | | | 123 | | | 124 | | |
| | | | 16 | | | 3 | | |
| | | | 440 | | | 600 | | |
| 3 | 128 | 129 | 130 | 131 | 132 | 133 | 134 | 135 |
| | 14 | 0 | 40 | 30 | 16 | 18 | 16 | 5 |
| | 1,700 | — | 400 | 740 | 1,200 | 220 | 1,070 | 1,300 |

What is claimed is:

1. In a method for labelling an organic compound selected from the group consisting of amino acids, peptides, nucleosides, sugars, aminosugars, amines and carboxylic acids, by the catalytic isotope exchange wherein said compound is reacted with tritium or deuterium, the improvement which comprises:
   (a) forming a solid phase mixture of said organic compound, or a complex of said organic compound with a platinum group metal, an inorganic carrier and a platinum group metal catalyst in an ampule;
   (b) evacuating said ampule and introducing gaseous tritium or deuterium at a pressure of up to 0.04 MPa;
   (c) heating said mixture up to a temperature of from 373° to 523° K., and maintaining the mixture at said temperature for 10 to 160 minutes;
   (d) cooling the mixture to a temperature of from 288° to 303° K.; and
   (e) thereafter isolating a labelled compound which is identical to said organic compound except for the exchanged isotope.

2. The method of claim 1, wherein in Step (a) a complex of said organic compound and a platinum group metal is prepared prior to forming the mixture.

3. The method of claim 1, wherein said inorganic carrier is selected from the group consisting of barium carbonate, barium sulfate, calcium carbonate, aluminum oxide and carbon.

* * * * *